United States Patent [19]

Brima

[11] Patent Number: 4,968,817
[45] Date of Patent: Nov. 6, 1990

[54] MANUFACTURE OF GAMMA-CROTONOLACTONE BY CARBONYLATION OF GLYCIDOL

[75] Inventor: Thomas S. Brima, Cincinnati, Ohio

[73] Assignee: National Distillers and Chemical Corporation, New York, N.Y.

[21] Appl. No.: 378,441

[22] Filed: Jul. 10, 1989

Related U.S. Application Data

[63] Continuation of Ser. No. 635,338, Jul. 27, 1984, abandoned.

[51] Int. Cl.$^5$ .................. C07D 307/04; C07D 307/26
[52] U.S. Cl. .................... 549/295; 549/313; 549/319
[58] Field of Search ................. 549/313, 295, 319

[56] References Cited

U.S. PATENT DOCUMENTS

| | | | |
|---|---|---|---|
| 2,359,208 | 9/1944 | Elderfield | 549/313 |
| 2,782,226 | 2/1957 | Seon et al. | 560/189 |
| 3,028,417 | 4/1962 | Eisenmann | 560/179 |
| 3,260,738 | 7/1966 | McClure et al. | 560/179 |
| 4,410,744 | 10/1983 | Campbell et al. | 549/313 |
| 4,451,407 | 5/1984 | Pesa et al. | 549/295 |

OTHER PUBLICATIONS

Houben-Weyl, Methoden der Organischen Chemie, vol. VI/2 (1963), pp. 571–572, 664.
R. Heck, Jour. Am. Chem. Soc., vol. 85 (1963), pp. 1460–1463.
Houben-Weyl, "Herstellung von Lactoner", Stuttgart: Tieme, 1963, pp. 571, 572, 664.

*Primary Examiner*—Glennon H. Hollrah
*Assistant Examiner*—Amelia A. Owens
*Attorney, Agent, or Firm*—Kenneth D. Tremain; Gerald A. Baracka

[57] ABSTRACT

A process for preparing a substituted or unsubstituted gamma-crotonolactone is provided which comprises reacting a substituted or unsubstituted glycidol of the formula:

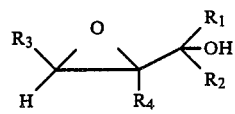

wherein $R_1$, $R_2$, $R_3$ and $R_4$ are the same or different and are H, alkyl of from 1 to 40 carbon atoms or aryl of from 6 to 18 carbon atoms, with carbon monoxide in the presence of a carbonylation catalyst to provide a corresponding beta-hydroxy lactone of the formula:

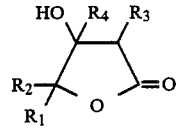

and dehydrating said beta-hydroxy lactone to provide the corresponding gamma-crotonolactone of the formula:

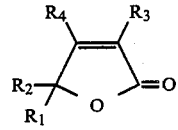

13 Claims, No Drawings

MANUFACTURE OF GAMMA-CROTONOLACTONE BY CARBONYLATION OF GLYCIDOL

This is a continuation of application Ser. No. 635,338, filed July 27, 1984, now abandoned.

FIELD OF THE INVENTION

This invention relates to a process for the manufacture of substituted or unsubstituted beta-hydroxy lactones and gamma-crotonolactones by carbonylation of glycidols. In addition, the invention provides a process for hydrogenating gamma-crotonolactones to provide the corresponding gamma-butyrolactones or tetrahydrofurans.

BACKGROUND OF THE INVENTION

Gamma-crotonolactone is commercially and industrially attractive for its potential as an intermediate in the manufacture of 1,4-butanediol and tetrahydrofuran. Gamma-crotonolactone is also useful as an organic intermediate and monomer for various polymerization reactions. Gamma-crotonolactone has been employed in the synthesis of methyl chrysanthemate which is a powerful insecticide, and the synthesis of cerulenin, an antibiotic and staganacin an anti-leukemia agent. Further, substituted crotonolactones are useful as cardiac glycosides and as agricultural chemicals.

A need exists for a commercially acceptable process for the production of gamma-crotonolactone that is direct and versatile in order to broaden its commercial availability.

Various prior art methods exist for the production of lactones, including, for example, the methods described in the following patents: U.S. Pat. Nos. 4,356,310; 4,175,089; 4,069,232 and 3,061,614. Various literature references disclose the catalytic carbonylation of epoxides in alcoholic solutions to form 3-hydroxy esters [e.g., Heck, R. F., *J. Am. Chem. Soc.*, Vol. 85, pp. 1460–1463 (1963)] and carbonylation of an epoxy olefinic compound to form lactones [e.g., Aumann, R., Ring, H., *Angew. Chem.*, Vol. 89, pp. 47–48 (1977)]. German Pat. No. 1,066,572 discloses carbonylation of trimethylene oxide to gamma-butyrolactone.

SUMMARY OF THE INVENTION

It is therefore an object of the invention to provide a direct and versatile process for the production of gamma-crotonolactones.

More particularly, it is an object of the present invention to provide a process for the production of substituted or unsubstituted gamma-crotonolactones by the carbonylation of the corresponding glycidols.

It is still a further object of the invention to provide a process for preparing beta-hydroxy lactones which can be readily converted to the corresponding gammacrotonolactones by dehydration procedures which are themselves well known in the art.

To achieve the objects in accordance with purposes of the invention as embodied and broadly described herein, the invention comprises a process for preparing a substituted or unsubstituted gamma-crotonolactone which comprises reacting a substituted or unsubstituted glycidol of the formula:

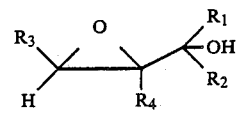

wherein $R_1$, $R_2$, $R_3$ and $R_4$ are the same or different and are H, alkyl of from 1 to 40 carbon atoms or aryl of from 6 to 18 carbon atoms, with carbon monoxide in the presence of a carbonylation catalyst to provide a corresponding beta-hydroxy lactone of the formula:

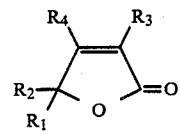

and dehydrating said beta-hydroxy lactone to provide the corresponding gamma-crotonolactone of the formula:

DETAILED DESCRIPTION OF THE PREFERRED EMBODIMENTS

In accordance with the present invention, a substituted or unsubstituted gamma-crotonolactone is prepared by reacting, in a suitable solvent, a substituted or unsubstituted glycidol of the formula:

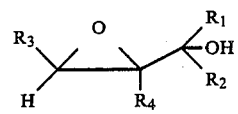

wherein $R_1$, $R_2$, $R_3$ and $R_4$ are the same or different and are H, alkyl of from 1 to 40 carbon atoms or aryl of from 6 to 18 carbon atoms, with carbon monoxide in the presence of a carbonylation catalyst. The $R_1$, $R_2$, $R_3$ and $R_4$ of the glycidol corresponds to $R_1$, $R_2$, $R_3$ and $R_4$ of the gamma-crotonolactone product. Preferably, $R_1$, $R_2$, $R_3$ and $R_4$ are the same or different and are H or methyl. To produce the more preferred unsubstituted gamma-crotonolactone $R_1$, $R_2$, $R_3$ and $R_4$ are all H.

Preferably, the carbonylation catalyst is a cobalt carbonyl. Other suitable catalysts include cobalt hydrocarbonyl and nickel compounds.

The gamma-crotonolactone produced preferably corresponds to the following formula:
wherein $R_1$, $R_2$, $R_3$ and $R_4$ will correspond to their respective identities from the glycidol starting material utilized.

The reaction of substituted or unsubstituted glycidol and carbon monoxide to provide beta-hydroxy lactone can take place over wide ranges of temperature and pressure in the presence or absence of solvent. The temperature of said reaction is about 25° C. to about 200° C. and preferably, from about 80° C. to about 160° C. The reaction will generally take place at a pressure of carbon monoxide of from atmospheric to about 4500 psig. Preferably, the pressure of carbon monoxide is from about 1000 to about 4000 psig. The time of reaction to achieve sufficient yield of products will depend, of course, on the particular reactants used and the temperature at which the reaction is carried out. Normally the reaction should proceed from about 2 to about 8 hours.

The reaction is advantageously carried out in any suitable solvent which will not interfere with the selective production of unsubstituted or substituted gammacrotonolactones. Preferred solvents include cyclic ethers such as tetrahydrofuran, tetrahydropyran and dioxane; acyclic ethers such as dimethoxyethane, diethylether; alkyl ethers of alkylene glycols and polyalkylene glycols such as methyl ethers of propylene glycol and di-, tri- and tetraethylene glycols; and the like. Mixtures of solvents can be employed.

Certain solvents have been found to affect the selectivity of the reaction to the lactone product. Use of acetone as solvent, for example, results in formation of dioxolane by-product derived from solvent interaction with glycidol. Similar results are obtained with methylethyl ketone. When pyridine was employed as solvent, no lactones were formed.

The beta-hydroxy lactone intermediate produced according to this reaction can readily be made to undergo dehydration to produce the corresponding unsubstituted or substituted gamma-crotonolactones. The conditions under which the intermediate will undergo such dehydration depends upon the particular reaction product. It has been found that when subjected to the conditions of gas-liquid chromatography (GLC) analysis, the substituted and unsubstituted beta-hydroxy lactones readily undergo dehydration to the corresponding gamma-crotonolactones. Generally, the dehydration can be accomplished by carrying out the reaction of glycidol and carbon monoxide in a dehydrating medium. Alternatively, the intermediate beta-hydroxy lactone can be dehydrated in a separate step employing a dehydrating agent such as a polyphosphoric acid.

The reaction sequence can be illustrated as follows:

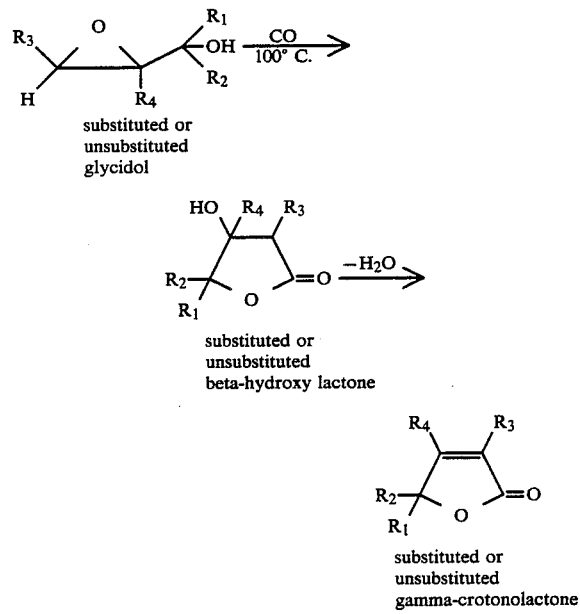

substituted or unsubstituted glycidol substituted or unsubstituted beta-hydroxy lactone substituted or unsubstituted gamma-crotonolactone Depending upon production economics, it may be advantageous to selectively catalytically hydrogenate the gamma-crotonolactone to provide gamma-butyrolactone, an important intermediate (e.g., for producing pyrrolidine) or tetrahydrofuran, another industrially important chemical, employing well known procedures.

The process of the invention is extremely versatile for producing various substituted gamma-crotonolactones, as will be illustrated by the following examples. The examples are not intended to be limiting of the scope of the present invention. In conjunction with the general and detailed description above, the examples provide further understanding of the present invention and outline preferred embodiments of the process of the invention.

The starting materials, solvents and reagents utilized in the examples whose method of preparation are not indicated, are commercially available compounds which would be available from chemical supply houses well known to the art such as Aldrich Chemical Company.

EXAMPLE 1

Unsubstituted gamma-crotonolactone is prepared as follows: Glycidol (25 g) and $Co_4(CO)_{12}$ (0.6 g) were placed in a 300 ml stirred reactor with tetrahydrofuran (100 ml) solvent. The reactor was then pressurized to 4000 psig with CO and heated at 100° C. for 8 hours. After cooling, the solvent was removed from the reaction mixture by means of an aspirator, and the concentrate was vacuum distilled to yield a low-boiling fraction containing crotonolactone (5.0 g) and 3-hydroxybutyrolactone (26.0 g, b.p. 115°–7° C./0.1 mmHg); the combined yield of lactones was 93%. Two drops of polyphosphoric acid were added to the 3-hydroxybutyrolactone (130 g, obtained from several runs) which was then vacuum distilled (160° C./13 mmHg). Water was then removed from the distillate by azeotropic distillation with chloroform; then the residue was fractionally distilled to obtain crotonolactone (103 g, 96% yield).

The reaction sequence of the above example is as follows:

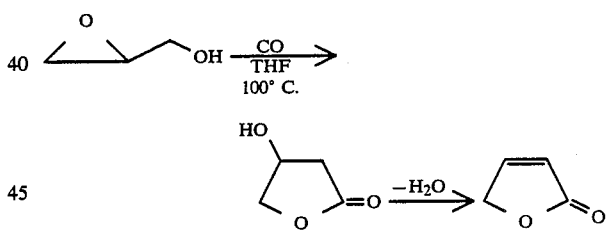

EXAMPLE 2

A mixture of glycidol (2.0 ml, 2.52 g), $Co_2(CO)_8$ (0.0204 g) and 5 ml tetrahydrofuran was placed in each of three 70 ml Parr bombs which were pressurized as follows:

Bombs 1 & 2 50 psig $H_2$ and 2950 psig CO
Bomb 3 3000 psig CO

Reactions were carried out at 100° C. with shaking for two hours (bombs 1 and 3) and four hours (bomb 2). The resulting products were analyzed by gas chromatography on a silar 10 CP column. Conversions of the glycidol charged and selectivities to lactones (δ-crotonolactone (minor) and 3-hydroxybutyrolactone) obtained were as given below:

| Bomb # | Reaction Time (hrs) | % Conversion of Glycidol | % Selectivity to Lactones |
|---|---|---|---|
| 1 | 2 | 89 | 93 |
| 2 | 4 | 97 | 70 |

| Bomb # | Reaction Time (hrs) | % Conversion of Glycidol | % Selectivity to Lactones |
|--------|---------------------|--------------------------|---------------------------|
| 3      | 2                   | 86                       | 94                        |

EXAMPLE 3

A mixture of glycidol (1.1 g), CO$_4$(CO)$_{12}$ (0.06 g) and 5 ml dimethoxyethane was placed in a 70 ml Parr bomb and pressurized to 3000 psig with CO. The reaction was carried out at 120° C. with shaking for 8 hours. An 87% yield of 3-hydroxybutyrolactone resulted.

EXAMPLE 4

4,4-Dimethylcrotonolactone is prepared from 3,4-epoxy-2-methyl-2-butanol which is readily obtained by epoxidation of 2-methyl-3-buten-2-ol with peracetic acid [G. B: Payne, *J. Am. Chem. Soc.*, 27, 3819 (1962)] or by the known epoxidation procedure of Itoh, et al. [*J. Am. Chem. Soc.*, 101, 165 (1979)].

A mixture of 3,4-epoxy-2-methyl-2-butanol (1.3 g, 13 mmoles) and CO$_4$(CO)$_{12}$ (0.06 g) in 5 ml tetrahydrofuran under 3500 psig (cold) CO was heated in a 70 ml Parr shaker bomb at 120° C. for 8 hours. Complete conversion was observed and 4,4-dimethyl-3-hydroxybutyrolactone (b.p. 145° C./1.75 mmHg) identified by C-13 NMR was obtained in 76% yield. It slowly underwent dehydration at room temperature to form 4,4-dimethylcrotonolactone (*Chem. Abstr.*, 5,5-dimethyl-2-furanone), identified by GC/MS and proton and C-13 NMR.

The reaction scheme is:

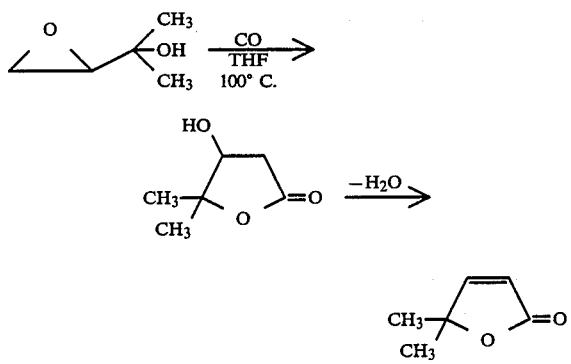

EXAMPLE 5

2-Methylcrotonolactone was prepared from 2,3-epoxybutan-1-ol obtained by epoxidation of 2-buten-1-ol according to Itoh, et al. (loc cit).

The substituted glycidol was carbonylated according to the procedure in Example 4. Approximately 80% of the glycidol was converted to form 2-methyl-3-hydroxybutyrolactone (60% yield), as identified by C-13 NMR. The compound underwent dehydration to form the 2-methylcrotonolactone (*Chem. Abstr.*, 3-methyl-2(5H)-furanone), identified by GC/MS. The reaction scheme is illustrated by:

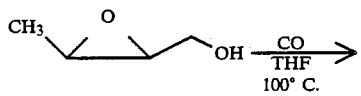

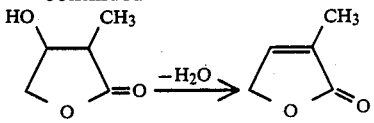

EXAMPLE 6

Glycidol (2 ml, 2.52 g), nickel acetylacetonate (0.0534 g) and 5 ml tetrahydrofuran were placed in a 70 ml Parr bomb. The bomb was pressurized with 3000 psig CO and heated at 100° C. with shaking for 4 hours. Analysis (gas chromatography on a silar 10 CP column) of the reaction mixture showed 80% glycidol conversion to 3-hydroxybutyrolactone lactone and δ-crotonolactone with a selectivity of 60%.

As is noted from the above examples, the process of the present invention provides for direct conversion of glycidol to crotonolactone. Furthermore, the versatility of the process can be appreciated from the ease with which substituted crotonolactones are produced from the corresponding substituted glycidols.

The scope of the present invention is not limited by the description, example, and suggested uses herein, and modification can be made without departing from the spirit of the invention. For example, an ethyl substituted crotonolactone can be produced by epoxidizing the corresponding ethyl substituted allyl alcohol by known methods and then carbonylating the so-formed substituted glycidol according to the process of the invention in a manner analogous to those preferred embodiments described above in the examples section to produce, for example, 3-ethyl-2(5H)-furanone. Thus, it is intended that the present invention cover the modifications and variations of this invention provided they come within the scope of the appended claims and their equivalents.

What is claimed is:

1. A process for preparing a gamma-crotonolactone of the formula

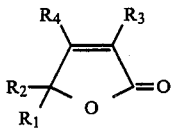

wherein R$_1$, R$_2$, R$_3$, and R$_4$ are the same or different and are hydrogen, an alkyl group having from 1 to 40 carbon atoms or an aryl group having from 6–18 carbon atoms which comprises reacting a glycidol of the formula

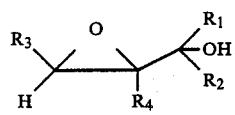

wherein R$_1$, R$_2$, R$_3$, R$_4$, are the same as defined above with carbon monoxide at a temperature from about 25° C. to 200° C. and pressure from atmospheric up to 4500 psig carbon monoxide in tetrahydrofuran and in the presence of a cobalt carbonyl or nickel compound catalyst to provide a corresponding beta-hydroxy lactone of the formula

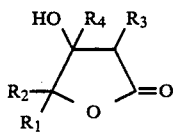

wherein $R_1$, $R_2$, $R_3$, and $R_4$ are the same as defined above and dehydrating said beta-hydroxy lactone to provide said gamma-crotonolactone.

2. The process of claim 1 wherein $R_1$, $R_2$, $R_3$ and $R_4$ are the same or different and are H or methyl.

3. The process of claim 1 wherein $R_1$, $R_2$, $R_3$ and $R_4$ are H.

4. The process of claim 1 wherein the reaction of glycidol and carbon monoxide is carried out at a temperature of from about 80° C. to about 160° C.

5. The process of claim 1 wherein the reaction of glycidol and carbon monoxide is carried out at a pressure of from about 1000 to about 4000 psig.

6. The process of claim 1 wherein dehydration is carried out in the presence of polyphosphoric acid or a sulfonated ion exchange resin.

7. The process of claim 1 wherein the reaction of glycidol and carbon monoxide is carried out for between about 2 to about 8 hours.

8. A process for preparing a beta-hydroxy lactone of the formula

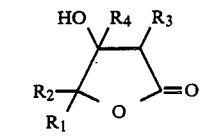

wherein $R_1$, $R_2$, $R_3$, and $R_4$ are the same or different and are hydrogen, an alkyl group having from 1 to 40 carbon atoms or an aryl group having from 6 to 18 carbon atoms which comprises reacting a glycidol of the formula

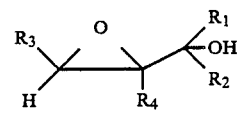

wherein $R_1$, $R_2$, $R_3$, and $R_4$ are the same as defined above with carbon monoxide at a temperature from about 25° C. to 200° C. and pressure from atmospheric up to 4500 psig carbon monoxide in tetrahydrofuran and in the presence of a cobalt carbonyl or nickel compound catalyst.

9. The process of claim 8 wherein $R_1$, $R_2$, $R_3$ and $R_4$ are the same or different and are H or methyl.

10. The process of claim 9 wherein $R_1$, $R_2$, $R_3$ and $R_4$ are H.

11. The process of claim 8 wherein the reaction is carried out at a temperature of from about 80° C. to about 160° C.

12. The process of claim 8 wherein the reaction is carried out at a pressure of from 1000 to about 4000 psig.

13. The process of claim 8 wherein the reaction is carried out for between about 2 to about 8 hours.

* * * * *

UNITED STATES PATENT AND TRADEMARK OFFICE
CERTIFICATE OF CORRECTION

PATENT NO. : 4,968,817
DATED : November 6, 1990
INVENTOR(S) : Thomas S. Brima

It is certified that error appears in the above-identified patent and that said Letters Patent is hereby corrected as shown below:

At column 2, line 15, the formula

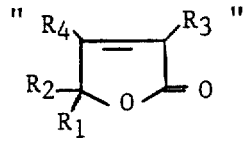

should read

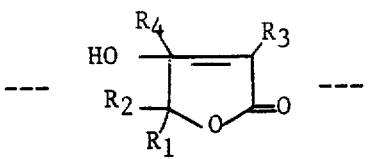

At column 2, line 23, the formula

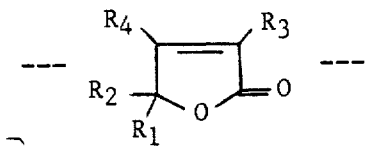

UNITED STATES PATENT AND TRADEMARK OFFICE
CERTIFICATE OF CORRECTION

Page 2 of 2

PATENT NO. : 4,968,817

DATED : November 6, 1990

INVENTOR(S) : Thomas S. Brima

It is certified that error appears in the above-identified patent and that said Letters Patent is hereby corrected as shown below:

should be inserted.

At column 5, line 23, the formula "$CO_4(CO)_{12}$" should read ---$Co_4(CO)_{12}$---

Signed and Sealed this

Twenty-first Day of July, 1992

Attest:

DOUGLAS B. COMER

*Attesting Officer*    *Acting Commissioner of Patents and Trademarks*